(12) United States Patent
Kim et al.

(10) Patent No.: US 11,964,666 B2
(45) Date of Patent: Apr. 23, 2024

(54) VEHICLE AND METHOD OF CONTROLLING THE SAME

(71) Applicants: HYUNDAI MOTOR COMPANY, Seoul (KR); KIA CORPORATION, Seoul (KR)

(72) Inventors: Kichang Kim, Suwon-si (KR); Dong Chul Park, Anyang-si (KR); Taekun Yun, Anyang-si (KR); Jinsung Lee, Hwaseong-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 392 days.

(21) Appl. No.: 17/387,136

(22) Filed: Jul. 28, 2021

(65) Prior Publication Data

US 2022/0135055 A1    May 5, 2022

(30) Foreign Application Priority Data

Nov. 4, 2020    (KR) .................... 10-2020-0145731

(51) Int. Cl.
*B60W 50/00*    (2006.01)
*A61B 5/00*    (2006.01)
(Continued)

(52) U.S. Cl.
CPC ....... *B60W 50/0098* (2013.01); *A61B 5/0205* (2013.01); *A61B 5/165* (2013.01);
(Continued)

(58) Field of Classification Search
CPC .................. B60W 50/0098; B60W 50/16; G06V 20/597; A61B 5/0205; A61B 5/165;
(Continued)

(56) References Cited

U.S. PATENT DOCUMENTS

2016/0001781 A1* 1/2016 Fung .................. G07C 9/37
701/36
2019/0332902 A1* 10/2019 Gallagher ............ G06V 10/811
(Continued)

FOREIGN PATENT DOCUMENTS

JP    H09206291 A    8/1997
KR    2017-0014050 A    2/2017
(Continued)

*Primary Examiner* — Yazan A Soofi
(74) *Attorney, Agent, or Firm* — MCDONNELL BOEHNEN HULBERT & BERGHOFF LLP

(57) ABSTRACT

A vehicle includes a plurality of sensors mounted on a seat, an output device, and a controller. The controller is configured to obtain an acceleration in each of a first seat in contact with a driver's back and a second seat in contact with a driver's thigh through the plurality of sensors, to determine a specific frequency in each of the first seat and the second seat, to determine contact pressure information and load information of each of the first seat and the second seat through the plurality of sensors, to determine a human vibration sensitivity using at least one of the specific frequency, the contact pressure information, and the load information, to determine driver's emotional information including positive emotional information and arousal emotional information based on the human vibration sensitivity, and to control the output device according to the driver's emotional information.

12 Claims, 20 Drawing Sheets

(51) Int. Cl.

| | |
|---|---|
| *A61B 5/0205* | (2006.01) |
| *A61B 5/024* | (2006.01) |
| *A61B 5/16* | (2006.01) |
| *A61B 5/18* | (2006.01) |
| *A61B 5/369* | (2021.01) |
| *B60N 2/00* | (2006.01) |
| *B60N 2/90* | (2018.01) |
| *B60W 50/14* | (2020.01) |
| *B60W 50/16* | (2020.01) |
| *G06V 20/59* | (2022.01) |

(52) U.S. Cl.
CPC .............. *A61B 5/18* (2013.01); *A61B 5/6893* (2013.01); *B60N 2/002* (2013.01); *B60W 50/16* (2013.01); *G06V 20/597* (2022.01); *A61B 5/024* (2013.01); *A61B 5/369* (2021.01); *B60N 2/976* (2018.02); *B60W 2050/143* (2013.01); *B60W 2540/22* (2013.01); *B60W 2540/221* (2020.02); *B60W 2540/223* (2020.02)

(58) Field of Classification Search
CPC ......... A61B 5/18; A61B 5/6893; A61B 2/002; A61B 50/16
USPC .......................................................... 701/36
See application file for complete search history.

(56) References Cited

U.S. PATENT DOCUMENTS

| | | | |
|---|---|---|---|
| 2019/0387998 A1* | 12/2019 | Garten | A61B 5/165 |
| 2021/0309252 A1* | 10/2021 | Boulanger | G06V 40/174 |
| 2021/0401340 A1* | 12/2021 | Gallagher | A61B 5/742 |
| 2022/0308195 A1* | 9/2022 | Zeng | G01S 13/003 |

FOREIGN PATENT DOCUMENTS

| | | |
|---|---|---|
| KR | 10-2020598 B1 | 9/2019 |
| KR | 2019-0131476 A | 11/2019 |
| KR | 10-2131391 B1 | 7/2020 |

* cited by examiner

FIG. 5B

| SECOND QUADRANT | FIRST QUADRANT |
|---|---|
| ○ STRONG VIBRATION<br>○ VIBRATION THAT DOES NOT CHANGE POSITION<br>○ FAST BEAT<br>○ VIBRATION WITHOUT LINEAR INCREASE / ATTENUATION | ○ CHANGE IN POSITION OF VIBRATION<br>○ STRONG VIBRATION<br>○ FAST BEAT<br>○ VIBRATION WITHOUT LINEAR INCREASE / ATTENUATION |
| THIRD QUADRANT | FOURTH QUADRANT |
| ○ CHANGE IN POSITION OF VIBRATION<br>○ WEAK VIBRATION<br>○ SLOW BEAT<br>○ BEFORE/AFTER VIBRATION, INCREASING INTENSITY / NO ATTENUATION PART, STARTING WITH VIBRATION WITH ATTACK AND STOPPING WITH ATTENUATION → INCREASING | ○ WEAK VIBRATION<br>○ CHANGE IN POSITION<br>○ SLOW BEAT<br>○ LINEAR INCREASE / ATTENUATION |

FIG. 7A

| | HALF FADE IN BEFORE VIBRATION | | | CHANGE IN POSITION OF VIBRATION | | | HALF FADE OUT BEHIND VIBRATION | |
|---|---|---|---|---|---|---|---|---|
| COMFORT | SHOULD INCREASE | | | INCREASE MUST CHANGE | | | SHOULD INCREASE | |
| INTERESTING | UNIT VIBRATION LENGTH | CHANGE IN POSITION OF VIBRATION | VIBRATION INTENSITY | VIBRATION INTENSITY | | | INTENSITY x FADE OUT | |
| | INCREASE SHOULD BE LONG | INCREASE MUST CHANGE | INCREASE SHOULD BE WEAK | INCREASE SHOULD BE WEAK | | | WHEN INTENSITY IS STRONG, IT INCREASES WHEN THERE IS NO FADE OUT WHEN INTENSITY IS WEAK, IT INCREASES WHEN THERE IS FADE OUT | |
| I WANT TO EXPERIENCE OFTEN | VIBRATION INTENSITY | | | FADE IN BEFORE VIBRATION X FADE OUT BEHIND VIBRATION | | | | |
| | INCREASE SHOULD BE WEAK | | | WHEN THERE IS NO FADE IN, FADE OUT SHOULD BE INCREASED WHEN THERE IS FADE IN, FADE OUT SHOULD BE INCREASED | | | | |
| RELIEVE STRESS | CHANGE IN POSITION OF VIBRATION | | | VIBRATION INTENSITY | | | | |
| | SHOULD INCREASE | | | INCREASE SHOULD BE WEAK | | | | |
| PREFERENCE | CHANGE IN POSITION OF VIBRATION | VIBRATION INTENSITY | | FADE IN BEFORE VIBRATION X CHANGE IN POSITION | | | | |
| | SHOULD INCREASE | INCREASE SHOULD BE WEAK | | WHEN THERE IS NO FADE IN, IT INCREASES GREATLY IF THERE IS CHANGE IN POSITION WHEN THERE IS FADE IN, IT INCREASES LITTLE IF THERE IS CHANGE IN POSITION | | | | |
| POSITIVED DEGREE OF EMOTION | CHANGE IN POSITION OF VIBRATION | | | VIBRATION INTENSITY | | | | |
| | SHOULD INCREASE | | | INCREASE SHOULD BE WEAK | | | | |
| AROUSED DEGREE OF EMOTION | CHANGE IN POSITION OF VIBRATION | VIBRATION INTENSITY | | CHANGE IN POSITION X FADE IN | | | VIBRATION INTENSITY X FADE OUT | |
| | SHOULD INCREASE | INCREASE SHOULD BE STRONG | | WHEN THERE IS NO CHANGE IN POSITION, FADE IN SHOULD BE INCREASED WHEN THERE IS CHANGE IN POSITION, FADE IN SHOULD BE INCREASED | | | WHEN INTENSITY IS STRONG, IT INCREASES WHEN THERE IS NO FADE IN WHEN INTENSITY IS WEAK, IT INCREASES WHEN THERE IS FADE IN | | though a pinrality of sensors, to determine a specific
VEHICLE AND METHOD OF CONTROLLING THE SAME

CROSS REFERENCE TO RELATED APPLICATIONS

This application is based on and claims priority under 35 U.S.C. § 119 to Korean Patent Application No. 10-2020-0145731, filed on Nov. 4, 2020, the disclosure of which is incorporated herein by reference.

BACKGROUND

1. Field

The disclosure relates to a vehicle and a method of controlling the vehicle.

2. Description of Related Art

Conventionally, a driver's emotion is estimated based on database of edge area, angle and distance information through image data analysis of a driver's motion.

However, when analyzing a posture while sitting in a driver's seat with an image, it is difficult to accurately recognize the driver's emotion when the driver's back and thighs are in close contact with the seat in addition to a motion of yawning or turning their head, and the decision is made with limited image information.

SUMMARY

An aspect of the disclosure is to provide a vehicle that measures a frequency and an acceleration in a seat on which a driver is seated, determines a human vibration sensitivity, determines emotional information of the driver according to the human vibration sensitivity, and controls an output device based thereon, and a method of controlling the vehicle.

Additional aspects of the disclosure will be set forth in part in the description which follows and, in part, will be obvious from the description, or may be learned by practice of the disclosure.

According to an aspect of the disclosure, there is provided a vehicle including a plurality of sensors mounted on a seat, an output device, and a controller configured to obtain an acceleration in each of a first seat in contact with a driver's back and a second seat in contact with a driver's thigh through the plurality of sensors, to determine a specific frequency in each of the first seat and the second seat, to determine contact pressure information and load information of each of the first seat and the second seat through the plurality of sensors, to determine a human vibration sensitivity using at least one of the specific frequency, the contact pressure information, and the load information, to determine driver's emotional information including positive emotional information and arousal emotional information based on the human vibration sensitivity, and to control the output device according to the driver's emotional information.

The controller may be configured to perform an emotional modeling based on the driver's emotional information.

The controller may be configured to perform the emotional modeling using a quadrant graph having the positive emotional information as a horizontal axis and the arousal emotional information as a vertical axis.

The controller may be configured to set a moving pattern in each quadrant of the quadrant graph so that the driver's emotional information changes to the positive emotional information.

In response to a case where the driver's emotional information is one of a pattern moving from a second quadrant to a first quadrant, a pattern moving from the second quadrant to a fourth quadrant, a pattern moving from a third quadrant to the first quadrant, and a pattern moving from the third quadrant to the fourth quadrant, the controller may be configured to determine that a driver's emotion changes to a positive emotion.

The controller may be configured to measure driver's electroencephalogram (EEG) information and a driver's heart rate.

The controller may be configured to reflect the EEG information and the heart rate to determine an emotional index of the emotional information.

The controller may be configured to determine that as the emotional index for the positive emotional information and the emotional index for the arousal emotional information are larger, the driver's emotional information is the positive emotional information, and to determine that as the emotional index for the positive emotional information and the emotional index for the arousal emotional information are smaller, the driver's emotional information is negative emotional information.

The output device may include at least one of a speaker, the seat, and a steering wheel.

The specific frequency may be a frequency sensitive to a human vibration.

According to another aspect of the disclosure, there is provided a method of controlling a vehicle including obtaining, by a controller, an acceleration in each of a first seat in contact with a driver's back and a second seat in contact with a driver's thigh through a plurality of sensors, determining, by the controller, a specific frequency in each of the first seat and the second seat, determining, by the controller, contact pressure information and load information of each of the first seat and the second seat through the plurality of sensors, determining, by the controller, a human vibration sensitivity using at least one of the specific frequency, the contact pressure information, and the load information, determining, by the controller, driver's emotional information including positive emotional information and arousal emotional information based on the human vibration sensitivity, and controlling, by the controller, an output device according to the driver's emotional information.

The method may further include performing, by the controller, an emotional modeling based on the driver's emotional information.

The method may further include performing, by the controller, the emotional modeling using a quadrant graph having the positive emotional information as a horizontal axis and the arousal emotional information as a vertical axis.

The method may further include setting, by the controller, a moving pattern in each quadrant of the quadrant graph so that the driver's emotional information changes to the positive emotional information.

The method may further include, in response to a case where the driver's emotional information is one of a pattern moving from a second quadrant to a first quadrant, a pattern moving from the second quadrant to a fourth quadrant, a pattern moving from a third quadrant to the first quadrant, and a pattern moving from the third quadrant to the fourth quadrant, determining, by the controller, that a driver's emotion changes to a positive emotion.

The method may further include measuring, by the controller, driver's electroencephalogram (EEG) information and a driver's heart rate.

The method may further include reflecting, by the controller, the EEG information and the heart rate to determine an emotional index of the emotional information.

The method may further include determining, by the controller, that as the emotional index for the positive emotional information and the emotional index for the arousal emotional information are larger, the driver's emotional information is the positive emotional information; and determining, by the controller, that as the emotional index for the positive emotional information and the emotional index for the arousal emotional information are smaller, the driver's emotional information is negative emotional information.

The output device may include at least one of a speaker, the seat, and a steering wheel.

The specific frequency may be the frequency sensitive to the human vibration.

BRIEF DESCRIPTION OF THE FIGURES

These and/or other aspects of the disclosure will become apparent and more readily appreciated from the following description of the embodiments, taken in conjunction with the accompanying drawings of which:

FIG. 5B is a table of emotional modeling of a vehicle driver according to an embodiment of the disclosure.

FIG. 7A is a table and FIG. 7B is a graph of emotional information of a vehicle driver according to an embodiment of the disclosure.

DETAILED DESCRIPTION

Figure 1:
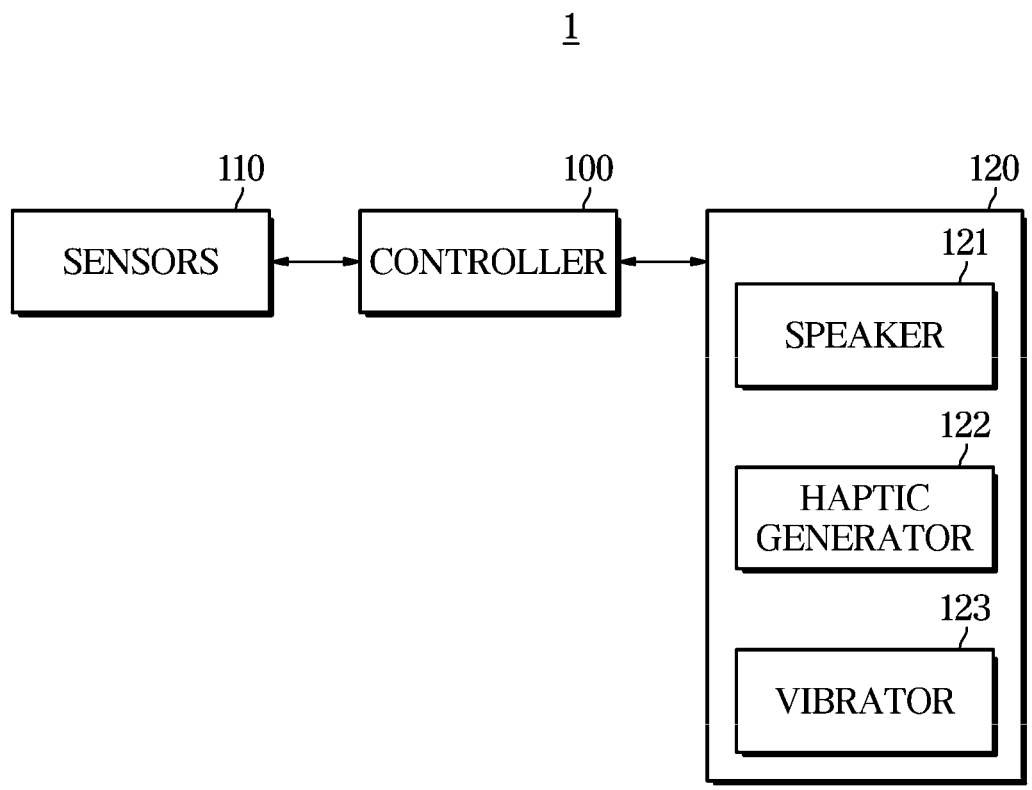
FIG. 1 is a control block diagram of a vehicle according to an embodiment of the disclosure.

Like reference numerals refer to like elements throughout the specification. Not all elements of the embodiments of the disclosure will be described, and the description of what are commonly known in the art or what overlap each other in the exemplary embodiments will be omitted. The terms as used throughout the specification, such as "~ part," "~ module," "~ member," "~ block," etc., may be implemented in software and/or hardware, and a plurality of "~ parts," "~ modules," "~ members," or "~ blocks" may be implemented in a single element, or a single "~ part," "~ module," "~ member," or "~ block" may include a plurality of elements.

It will be further understood that the term "connect" and its derivatives refer both to direct and indirect connection, and the indirect connection includes a connection over a wireless communication network.

The terms "include (or including)" and "comprise (or comprising)" are inclusive or open-ended and do not exclude additional, unrecited elements or method steps, unless otherwise mentioned.

Further, when it is stated that a layer is "on" another layer or substrate, the layer may be directly on another layer or substrate or a third layer may be disposed therebetween.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

It is to be understood that the singular forms "a," "an," and "the" include plural references unless the context clearly dictates otherwise.

Reference numerals used for method steps are merely used for convenience of explanation, but not to limit an order of the steps. Thus, unless the context clearly dictates otherwise, the written order may be practiced otherwise.

Hereinafter, an operation principle and embodiments of the disclosure will be described with reference to accompanying drawings.

FIG. 1 is a control block diagram of a vehicle according to an embodiment of the disclosure. FIG. 2 is an interior view of a vehicle and a graph of a human vibration sensitivity for determining the human vibration sensitivity of the vehicle according to an embodiment of the disclosure.

Referring to FIGS. 1 and 2, a vehicle 1 may include a plurality of sensors 110, an output device 120, and a controller 100 mounted on a seat.

The controller 100 may obtain an acceleration from each of a first seat contacted by a driver's back and a second seat contacted by a driver's thigh through the plurality of sensors 110, determine a specific frequency in each of the first and second seats, determine contact pressure information and load information of each of the first seat and the second seat through the plurality of sensors 110, determine a human vibration sensitivity using at least one of the specific frequency, the contact pressure information, and the load information, determine a driver's emotional information including positive emotional information and arousal emotional information based on the human vibration sensitivity, and control the output device 120 according to the driver's emotional information.

The plurality of sensors 110 may be mounted on the seat of the vehicle 1, and may be a 4-axis accelerometer and a contact pressure measuring device, but the disclosure is not limited thereto.

Figure 2A:
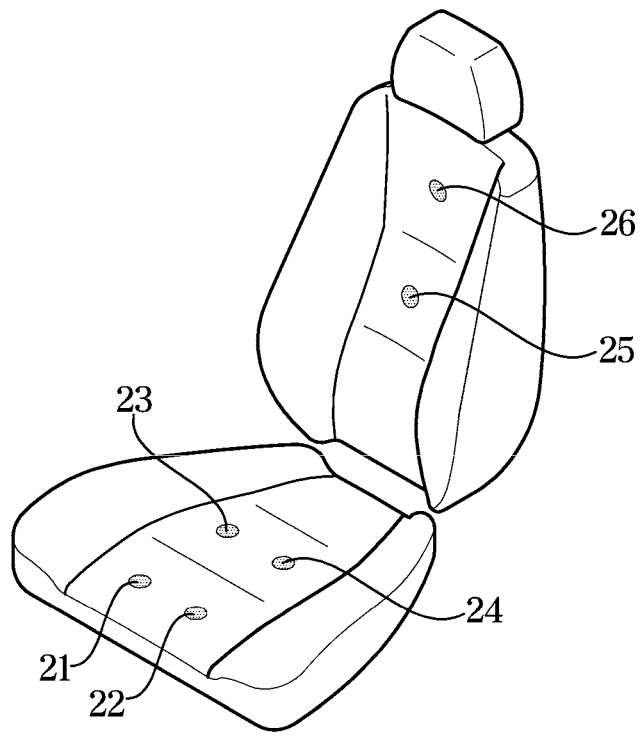
FIG. 2A is an interior view of a vehicle and FIG. 2B is a graph of a human vibration sensitivity for determining the human vibration sensitivity of the vehicle according to an embodiment of the disclosure.

Referring to FIG. 2A, two sensors 25 and 26 may be mounted on the first seat that is in contact with the driver's back, and may be mounted one at a top and one at a bottom based on a center of the first seat. However, a number of attachments and attachment positions of the sensors 110 are not particularly limited.

Referring to FIG. 2A, four sensors 21, 22, 23, and 24 may be mounted on the second seat that is in contact with the driver's thigh, and one may be mounted on each of upper, lower, left, and right sides based on a center of the second seat. However, the number of attachments and the attachment positions of the sensors 110 are not particularly limited.

The controller 100 may determine a resonance frequency and a vibration sensitivity using the frequency and the acceleration.

Figure 2B:
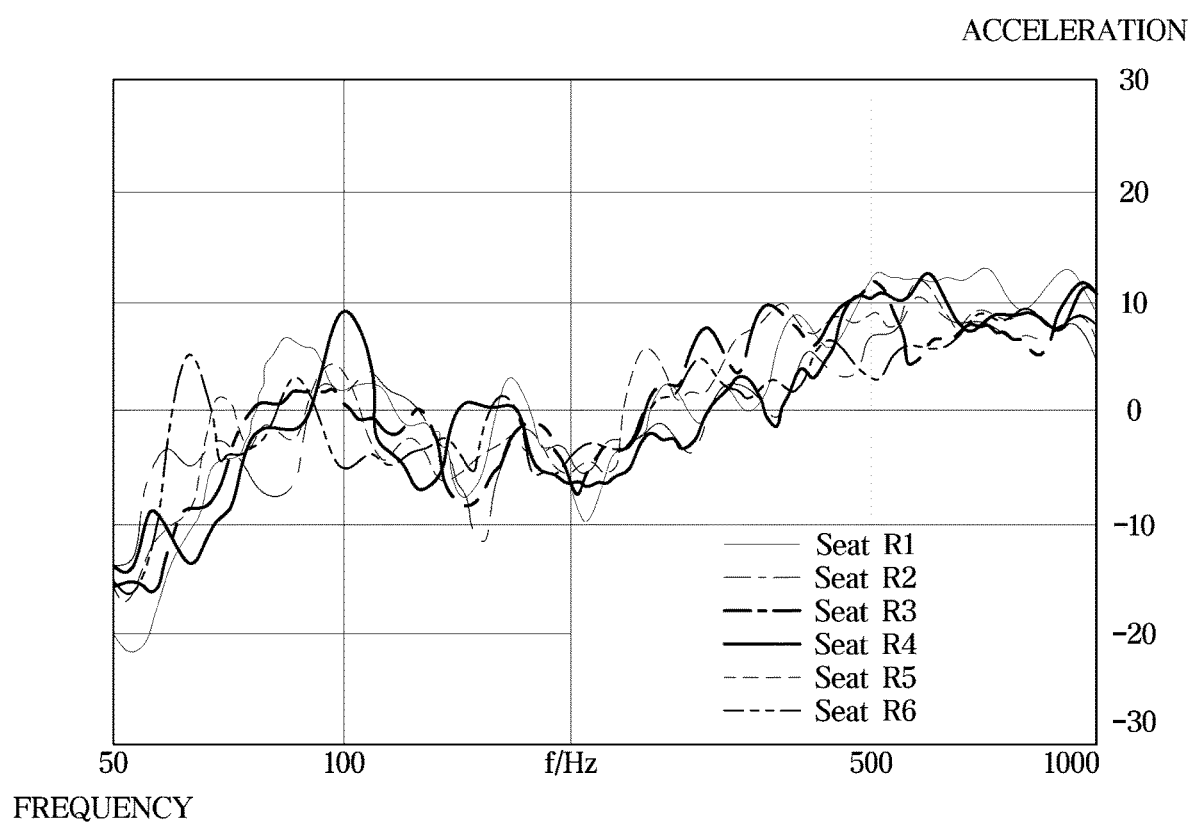

Referring to FIG. 2B, the acceleration may be obtained from each of the plurality of sensors 21, 22, 23, 24, 25, and 26, and the vibration sensitivity corresponding to the plurality of sensors 21, 22, 23, 24, 25, and 26 may be determined by using a change in acceleration according to the frequency in each of the plurality of sensors 21, 22, 23, 24, 25, and 26.

FIG. 3 is a view and a graph for determining a seat contact pressure and a load of a vehicle according to an embodiment of the disclosure.

Figure 3A:
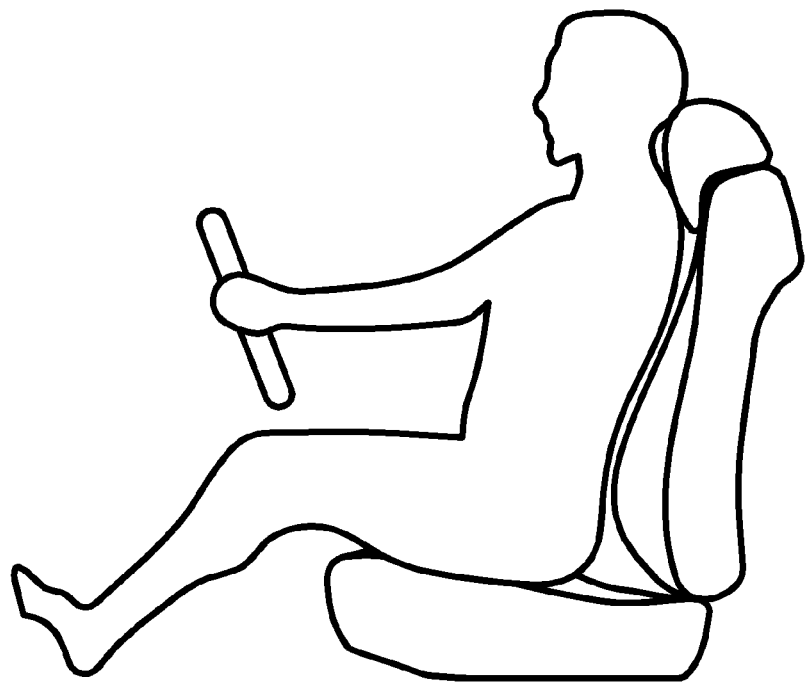
FIGS. 3A, 3B, 3C, and 3D are views
Figure 3B:
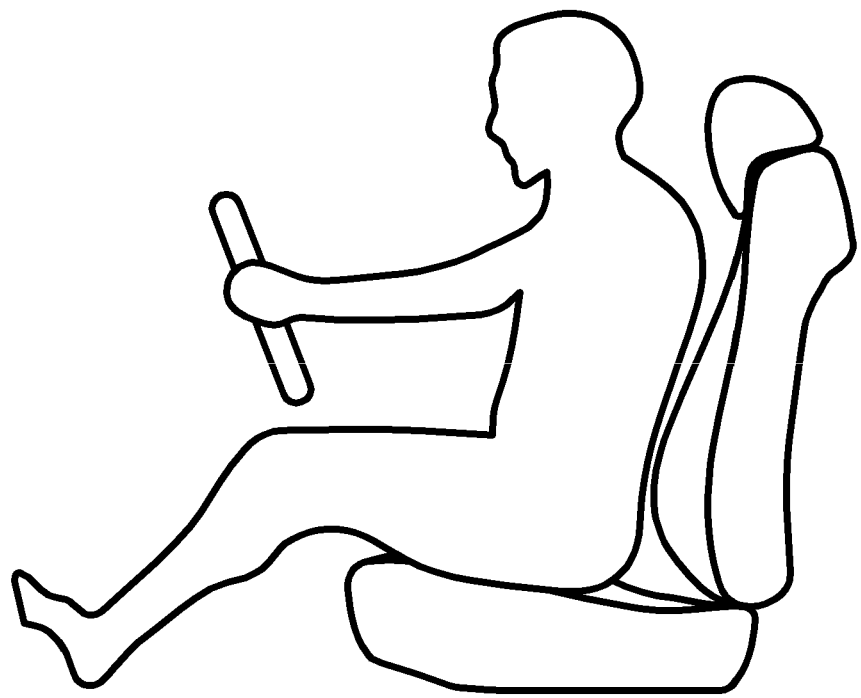

FIG. 3A is a view illustrating a state in which the driver is seated with the back and thighs in close contact with the seat, and FIG. 3B is a view illustrating a state in which the driver is seated in close contact with the seat with only the thighs and without the back.

Figure 3C:
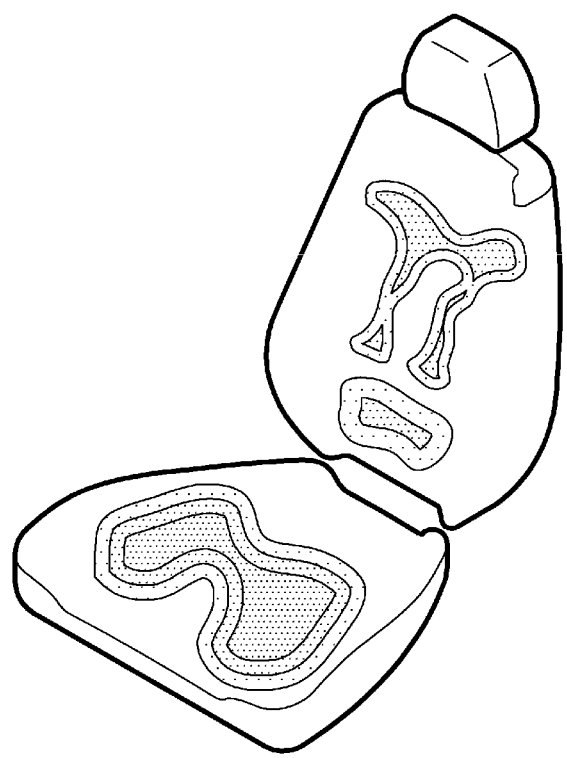

FIG. 3C is a view illustrating a state in which a pressure is distributed on a seat contact and a load is distributed to the seat contact when the driver sits in close contact with the back and thighs to the seat.

Figure 3D:
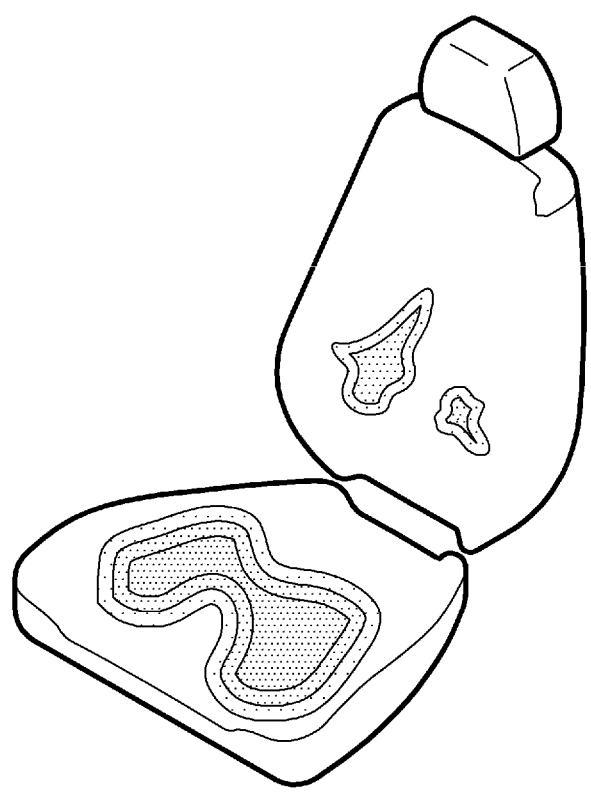
Figure 3E:
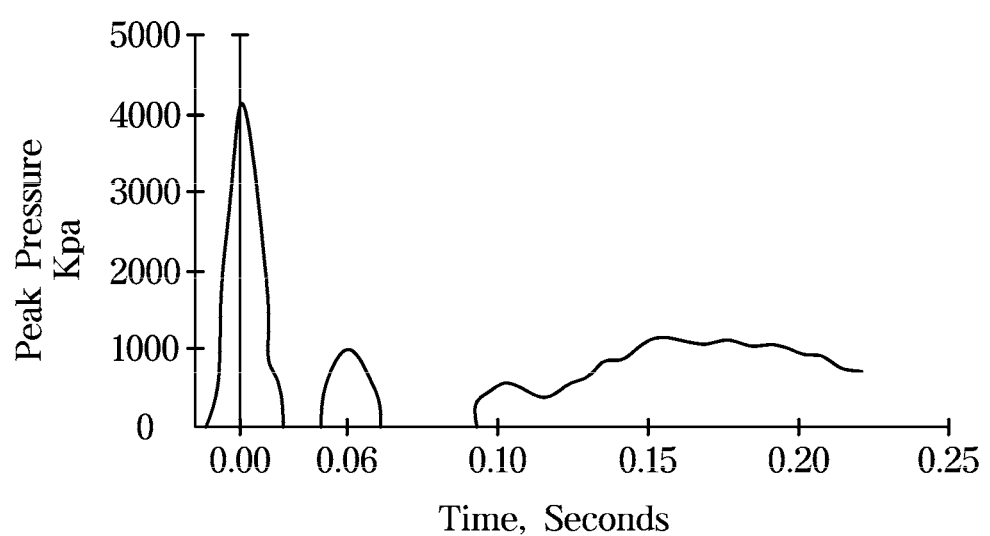
FIG. 3E is a graph for determining a seat contact pressure and a load of a vehicle according to an embodiment of the disclosure.

FIG. 3D is a view illustrating a state in which the pressure is distributed on the seat contact and the load is distributed to the seat contact when the driver sits in close contact with the seat with only the thighs and without the back. In this case, FIG. 3E illustrates a graph of the contact pressure over time.

Here, the controller 100 may measure the pressure on the seat contact from each of the plurality of sensors 21, 22, 23, 24, 25, and 26 in order to analyze the load on the seat contact.

The controller 100 may determine the specific frequency sensitive to a human vibration in each of the first seat contacted by the driver's back and the second seat contacted by the driver's thigh. For example, the specific frequency may be 50 Hz, 70 Hz, 90 Hz, or 110 Hz, but is not limited thereto.

The controller 100 may obtain a maximum contact pressure value of each of the first seat contacted by the driver's back and the second seat contacted by the driver's thigh.

The controller 100 may determine the human vibration sensitivity, using a frequency sensitive to the human vibration, the contact pressure information, and the load information. In more detail, the controller 100 may determine the human vibration sensitivity by determining a change in a perceived intensity according to a vibration amplitude for each of 50 Hz, 70 Hz, 90 Hz, and 110 Hz, which are specific frequencies sensitive to the human vibration.

The controller 100 may perform emotional modeling based on the positive emotional information and the arousal emotional information.

In more detail, the controller 100 may perform a driver's emotional modeling using a quadrant graph having the positive emotional information as a horizontal axis and the arousal emotional information as a vertical axis. The controller 100 may perform the emotional modeling by setting a moving pattern in each quadrant of the quadrant graph so that the driver's emotional information changes to the positive emotional information.

The controller 100 may determine driver's electroencephalogram (EEG) information and a heart rate variability (HRV).

The controller 100 may perform an emotional index analysis of the driver's emotional information by reflecting the driver's EEG information and the HRV.

The controller 100 may use a Frontal Alpha Asymmetry (FAA)-Valence analysis method as a measure of a positive emotion among the driver's emotional information for the emotional index analysis. In this case, the FAA-Valence analysis method may be a phenomenon in which an activity of an alpha band EEG in a frontal lobe illustrates asymmetry in left and right hemispheres.

In addition, the controller 100 may use a Frontal Theta Differential Entropy (FTDE)-Arousal analysis method as a measure of an arousal emotion among the driver's emotional information for the emotional index analysis. In this case, the FTDE-Arousal analysis method may represent a differential entropy value of a brain signal in theta band (4 to 8 Hz) in a central part of the frontal lobe of the driver.

The controller 100 may use an HRV analysis method to determine a driver's heart rate fluctuation. In this case, HRV may refer to a variation in time interval between adjacent heartbeats.

The controller 100 may control the output device 120 based on at least one of the driver's emotional information, emotional modeling, and emotional index.

Referring again to FIG. 1, the controller 100 may control a speaker 121 to output a sound in order to change the driver's emotion into the positive emotion.

The controller 100 may control a haptic generator 122 and a vibrator 123 to change the driver's emotion into the positive emotion, and control the output of ultrasonic waves or vibrations. Here, the vibrator 123 may include an actuator, the plurality of vibrators 123 may be mounted on the seat of the vehicle 1.

The controller 100 may simultaneously output sound, vibration, and ultrasound, and may automatically output the sound, the vibration, and the ultrasound by setting an output time of the sound, the vibration, and the ultrasound based on the driver's emotional information and emotional modeling.

The controller 100 may smoothly control a steering wheel of the vehicle 1 so that the driver's emotion changes into the positive emotion.

The controller 100 may include a non-transitory memory storing an algorithm to control operation of the components in the vehicle 1 or data about a program that implements the algorithm, and a processor carrying out the aforementioned operation using the data stored in the memory. The memory and the processor may be implemented in separate chips. Alternatively, the memory and the processor may be implemented in a single chip.

A storage may correspond to a memory that stores the above-mentioned information and information described later. In order to store various types of information, the storage may be implemented with at least one of the non-volatile memory device, such as cache, read only memory (ROM), programmable ROM (PROM), erasable programmable ROM (EPROM), electrically erasable programmable ROM (EEPROM), a volatile memory device, such as random access memory (RAM), or a storage medium, such as a hard disk drive (HDD) or a compact disk (CD) ROM, without being limited thereto.

Figure 4A:
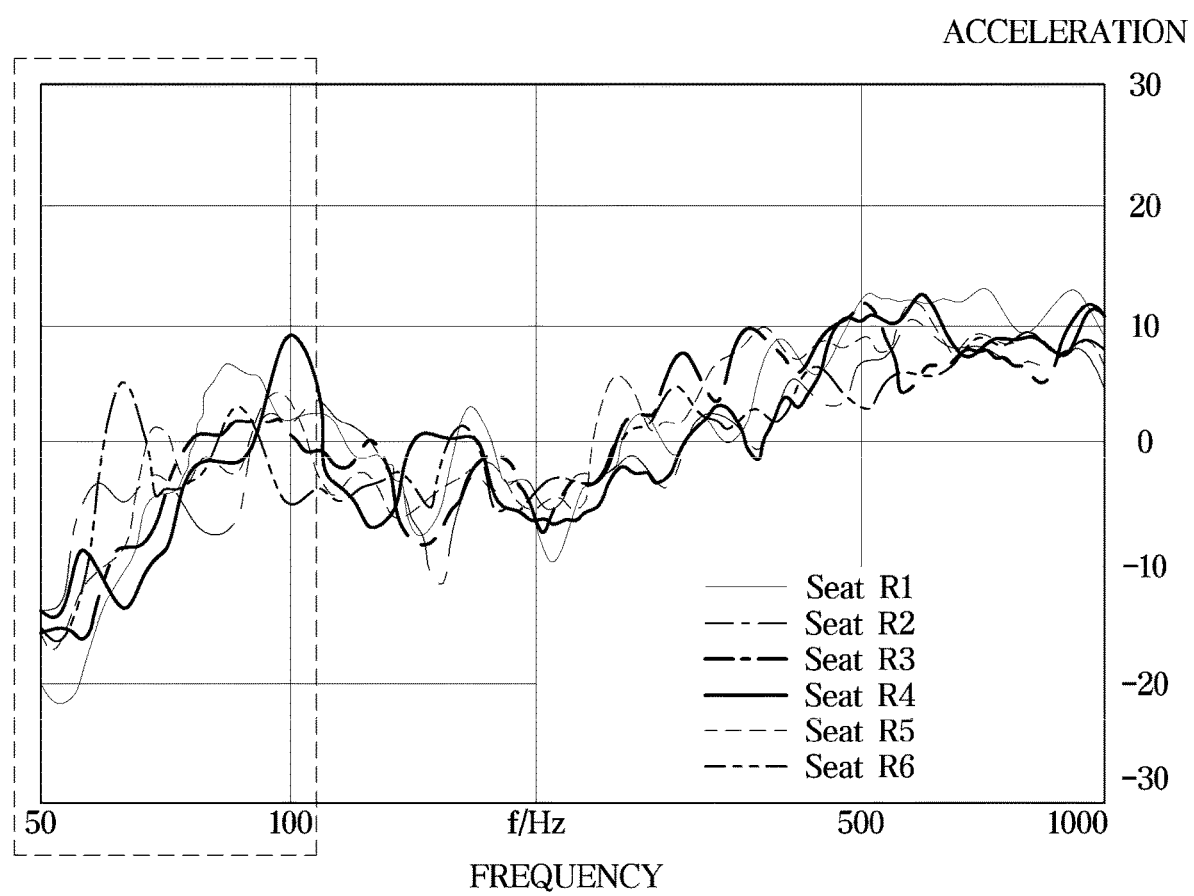
FIGS. 4A, 4B, and 4C are views illustrating a perceived intensity according to a specific frequency of a vehicle seat according to an embodiment of the disclosure.
Figure 4B:
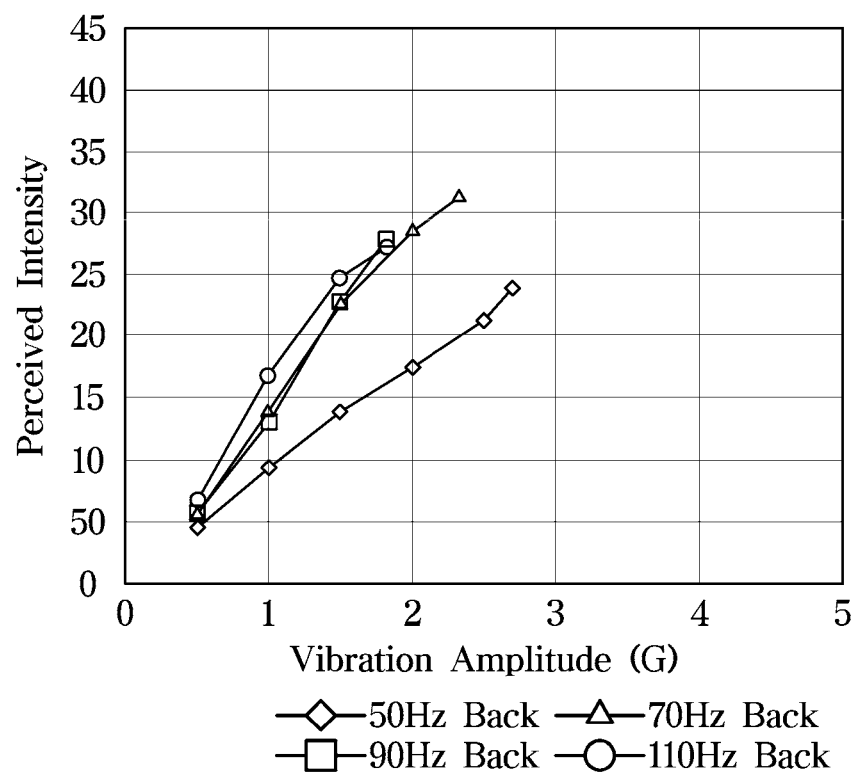
Figure 4C:
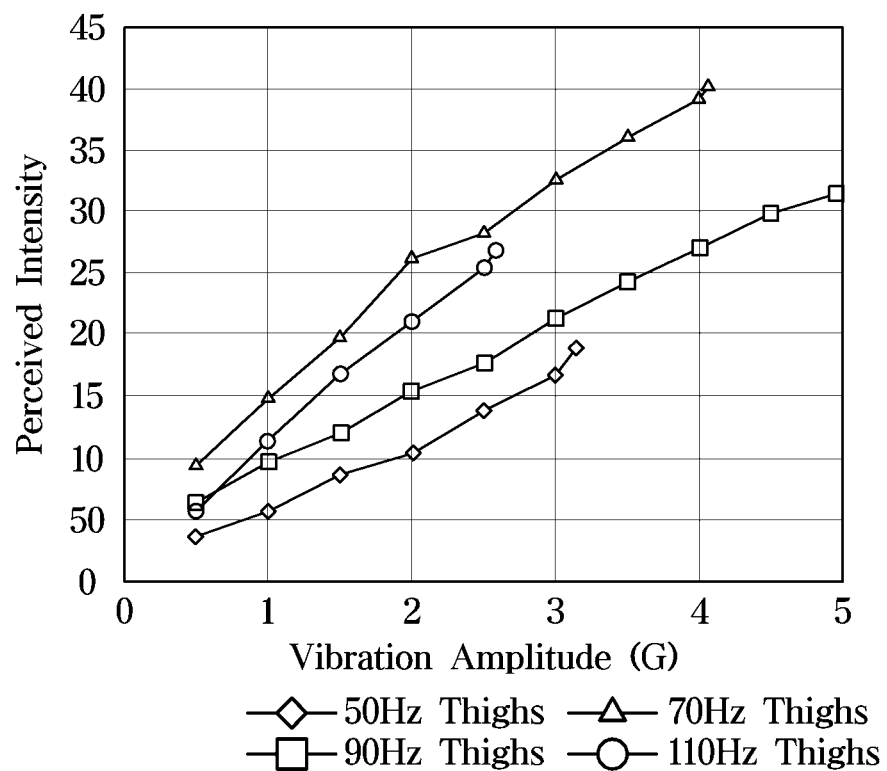

FIGS. 4A, 4B, and 4C are views illustrating a perceived intensity according to a specific frequency of a vehicle seat according to an embodiment of the disclosure.

Referring to FIG. 4A, a low frequency, which is a frequency sensitive to the human vibration, may be identified in each of the first seat contacted by the driver's back and the second seat contacted by the driver's thigh. For example, frequencies sensitive to the human vibration may be 50 Hz, 70 Hz, 90 Hz, and 110 Hz, but are not limited thereto.

Referring to FIGS. 4B and 4C, the change in the perceived intensity according to the vibration amplitude for each of 50 Hz, 70 Hz, 90 Hz, and 110 Hz, which are the frequencies sensitive to the human vibration, may be identified, and the human vibration sensitivity may be identified.

In more detail, referring to FIG. 4B, the human vibration sensitivity for the first seat may be identified based on the contact pressure information, the load information, and the frequency sensitive to the human vibration of the first seat that the driver's back is in contact with.

In addition, referring to FIG. 4C, the human vibration sensitivity for the second seat may be identified based on the contact pressure information, the load information, and the frequency sensitive to the human vibration of the second seat that the driver's thigh contacts with.

Figure 5A:
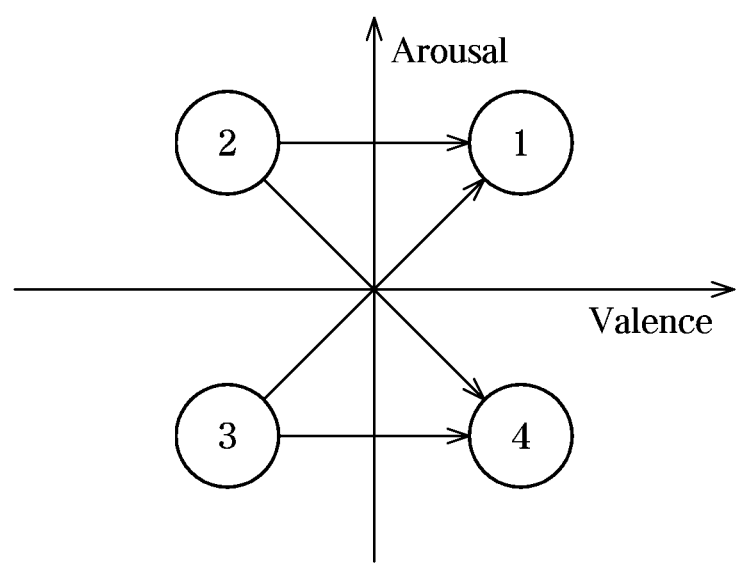
FIGS. 5A and 5C are graphs.
Figure 5C:
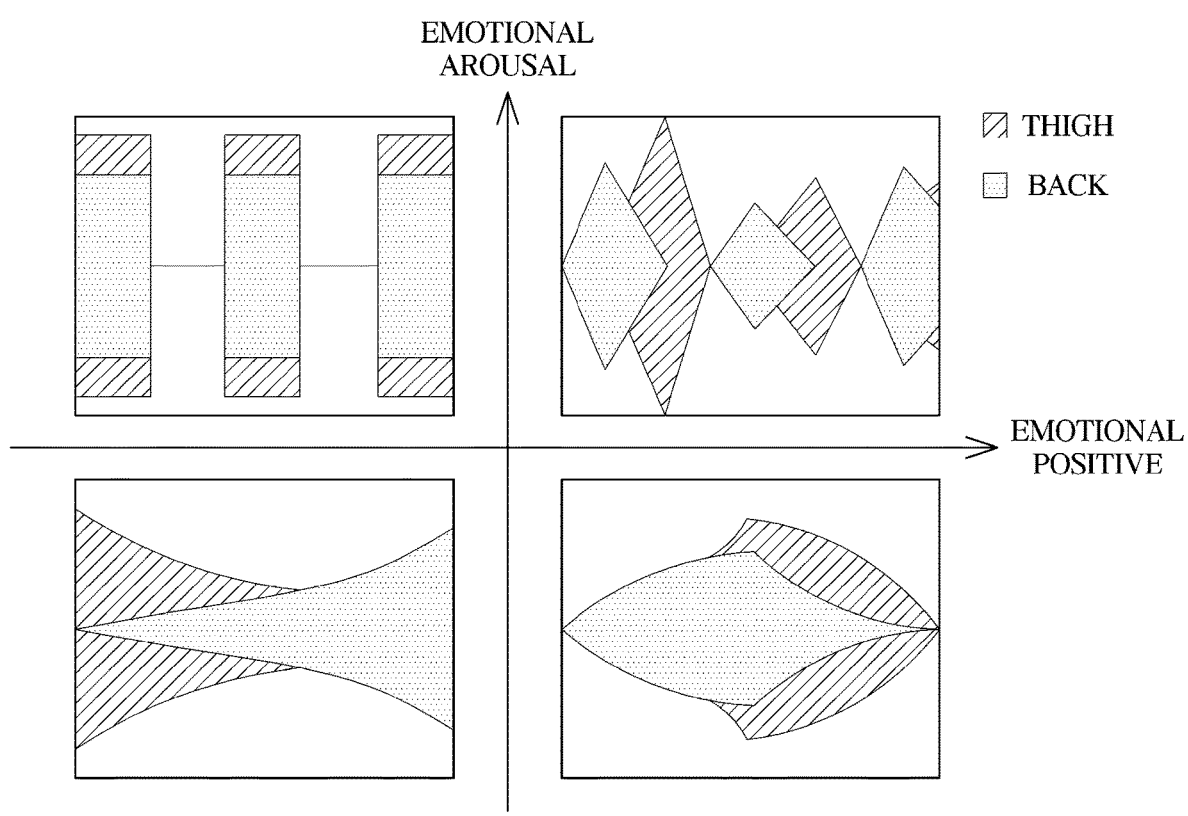

FIGS. 5A and 5C are graphs of emotional modeling of a vehicle driver according to an embodiment of the disclosure.

The vehicle 1 may perform the emotional modeling based on driver's emotional information including the positive emotional information and the arousal emotional information of the driver.

In more detail, the vehicle 1 may perform the driver's emotional modeling based on the quadrant graph having the positive emotional information as the horizontal axis and the arousal emotional information as the vertical axis.

The vehicle 1 may perform the emotional modeling by setting the moving pattern in each quadrant of the quadrant graph so that the driver's emotional information changes to the positive emotional information.

Conventionally, in order to recognize a driver's facial expression and determine the driver's emotion, a separate camera device was required, and there is a problem in that it is limited in accurately determining the driver's emotion due to a large error range.

In an embodiment of the disclosure, in order to determine the emotion based on the driver's voice, for example, cough, song, laughter, cry, etc., a configuration for determining a change in the driver's emotion according to a music pattern and performing an emotion determination according to the driver's voice and a seating posture is disclosed.

For example, referring to FIG. 5A, when it is determined that the driver's emotional information is in a second quadrant or a third quadrant of an emotional modeling graph, the vehicle 1 may determine that the driver is in a negative emotional state. When it is determined that the driver's emotional information is in a first quadrant or a fourth quadrant of an emotional modeling graph, the vehicle 1 may determine that the driver is in a positive emotional state.

For example, referring to FIG. 5A, the vehicle 1 illustrates four patterns for determining the driver's emotions based on deep learning.

In a case of a pattern moving from the second quadrant to the first quadrant, a pattern moving from the second quadrant to the fourth quadrant, a pattern moving from the third quadrant to the first quadrant, and a pattern moving from the third quadrant to the fourth quadrant by reflecting the positive emotional information and the arousal emotional information, the vehicle 1 may determine the change from the driver's emotion into the positive emotion.

For example, FIG. 5B is a table illustrating a method of outputting the sound and the vibration for changing the driver's emotion based on the deep learning into the positive emotion.

When the vehicle 1 outputs the sound and the vibration at the same time, it may be determined that the driver's emotion changes into the positive emotion.

In more detail, referring to FIG. 5B, when the vehicle 1 controls the output device 120 so that a position change of the vibration is large, an intensity of the vibration is large, and a beat of the sound is fast, it may be determined that the driver's positive emotion and arousal emotion increase. At this time, referring to FIG. 5C, a portion where a linearity increases and attenuates may be determined as the driver's positive emotion. For example, the driver may be in an emotional state, such as likes, wants to feel more often, is comfortable, or is satisfied.

In addition, referring to FIG. 5B, when the vehicle 1 controls the output device 120 so that the position change of the vibration is small, the intensity of the vibration is large, and the beat of the sound is fast, it may be determined that the driver's positive emotion decreases and the driver's arousal emotion increases. In this case, referring to FIG. 5C, it may be a constant vibration in which the linearity does not increase or decrease.

In addition, referring to FIG. 5B, when the vehicle 1 controls the output device 120 so that the position change of the vibration is large, the intensity of the vibration is small, and the beat of the sound is slow, it may be determined that the driver's positive emotion and arousal emotion decrease.

For example, when describing the change in the driver's emotions according to the sound output from the speaker 121, in order to perform a pattern moving from the third quadrant to the first quadrant, the vehicle 1 may transmit a clear melody using smoothly continuous notes and pull sounds, use simple, bright, warm, and soft chords, and output a first sound using various musical instruments such as acoustic instruments with a bright and clear feeling like a piano.

In addition, in order to perform a pattern moving from the second quadrant to the fourth quadrant, the vehicle 1 may use a stable chord with a slow tempo, bright and comfortable feeling, clearly distinguish between a melody and accompaniment by limiting a number of piano arpeggio (feeling of a calm wave), a music played by string instruments with a long note length, and a number of instruments, and output a second sound using a beach wave sound ASMR.

Figure 6A:
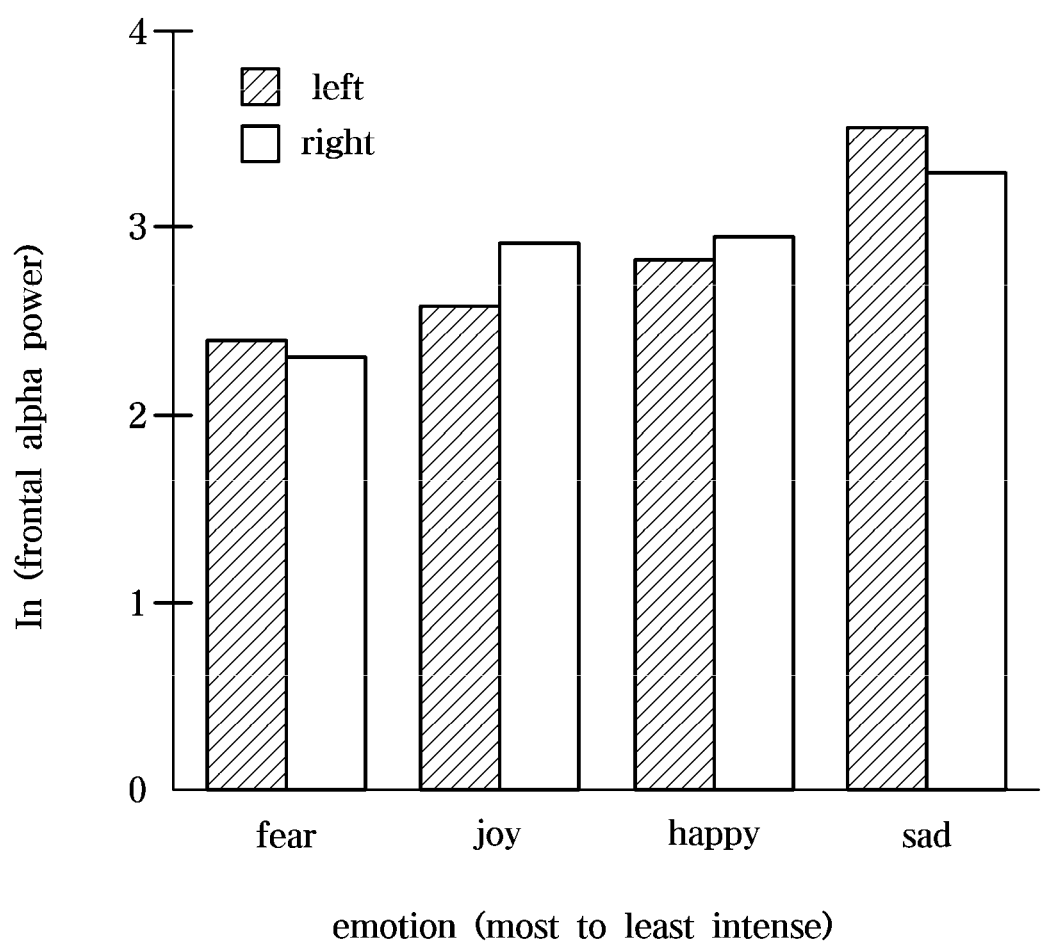
FIGS. 6A and 6B are graphs of an emotional index of a vehicle driver according to an embodiment of the disclosure.
Figure 6B:
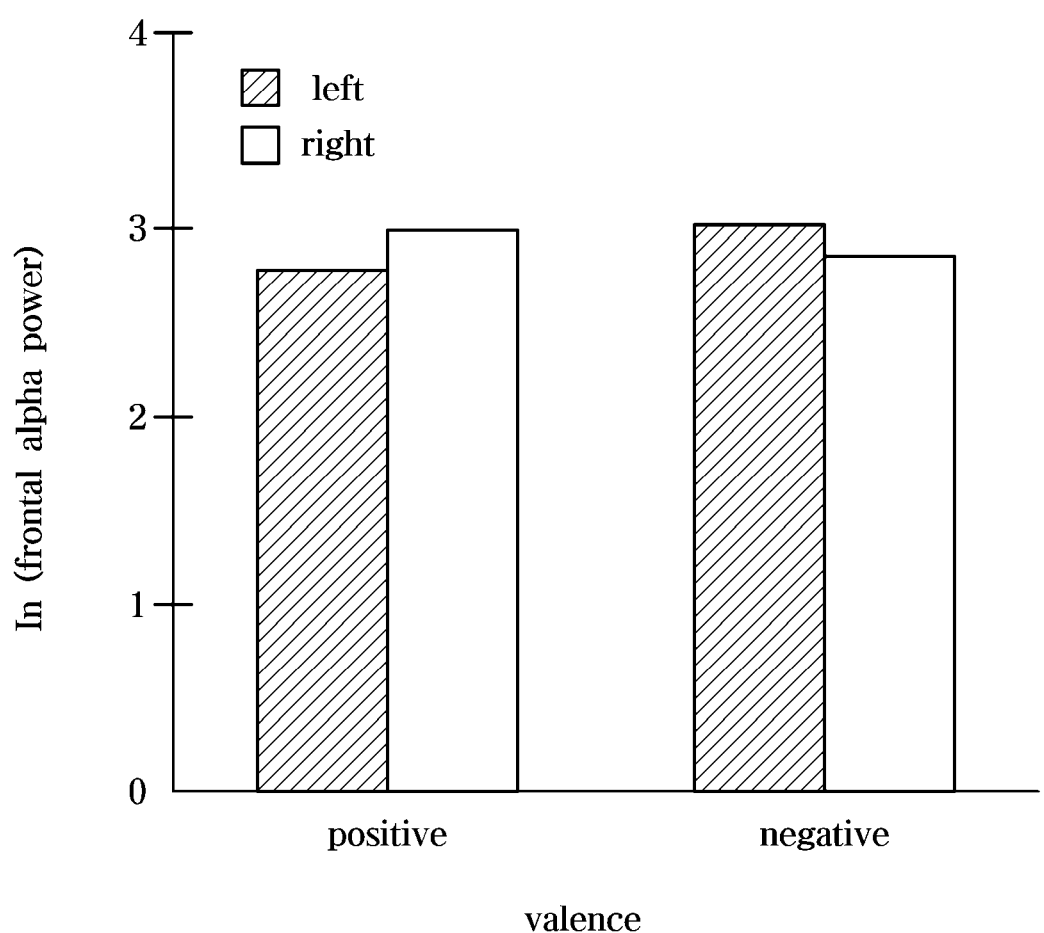

In addition, for a four quadrant fixed pattern, the vehicle 1 may output a third sound using a combination of a slow tempo, a repetitive rhythm pattern to provide a stable and comfortable feeling, a soft, clear and bright sound of the piano, a bird sound, a forest sound, a melody line that connects long and smoothly, and a note FIGS. 6A and 6B are graphs of an emotional index of a vehicle driver according to an embodiment of the disclosure.

Referring to FIG. 6A, the horizontal axis may represent the emotions of happiness, joy, sadness, and fear corresponding to the driver's emotional information, and the vertical axis is the driver's EEG information, which may be a value obtained by comparing and evaluating an index for an alpha band EEG activity in the frontal lobe with the value between 1 and 4. Referring to FIG. 6B, the horizontal axis may indicate the positive emotional information, and the vertical axis may indicate the driver's EEG information, which may be a value obtained by comparing and evaluating the index for the alpha band EEG activity in the frontal lobe with the value between 1 and 4.

In this case, it may refer to that the larger the value of the EEG information, the larger the variation in the driver's relative emotions.

Here, the emotional index analysis was performed using the FAA (Frontal Alpha Asymmetry)-Valence analysis, and the FAA-Valence analysis was a phenomenon in which the alpha band EEG activity in the frontal lobe showed asymmetry in the left and right hemispheres. It can be used as a measure of positive emotional information of information.

On the other hand, to improve an accuracy of the driver's emotional index, the FTDE-Arousal analysis method may be used, and the FTDE-Arousal analysis method may represent the differential entropy value of the brain signal in theta band (4 to 8 Hz) in the central part of the frontal lobe of the driver. A Theta activity in a brain region may be used as a measure of the arousal emotional information of the emotional information according to the driver's seating posture.

Figure 7B:
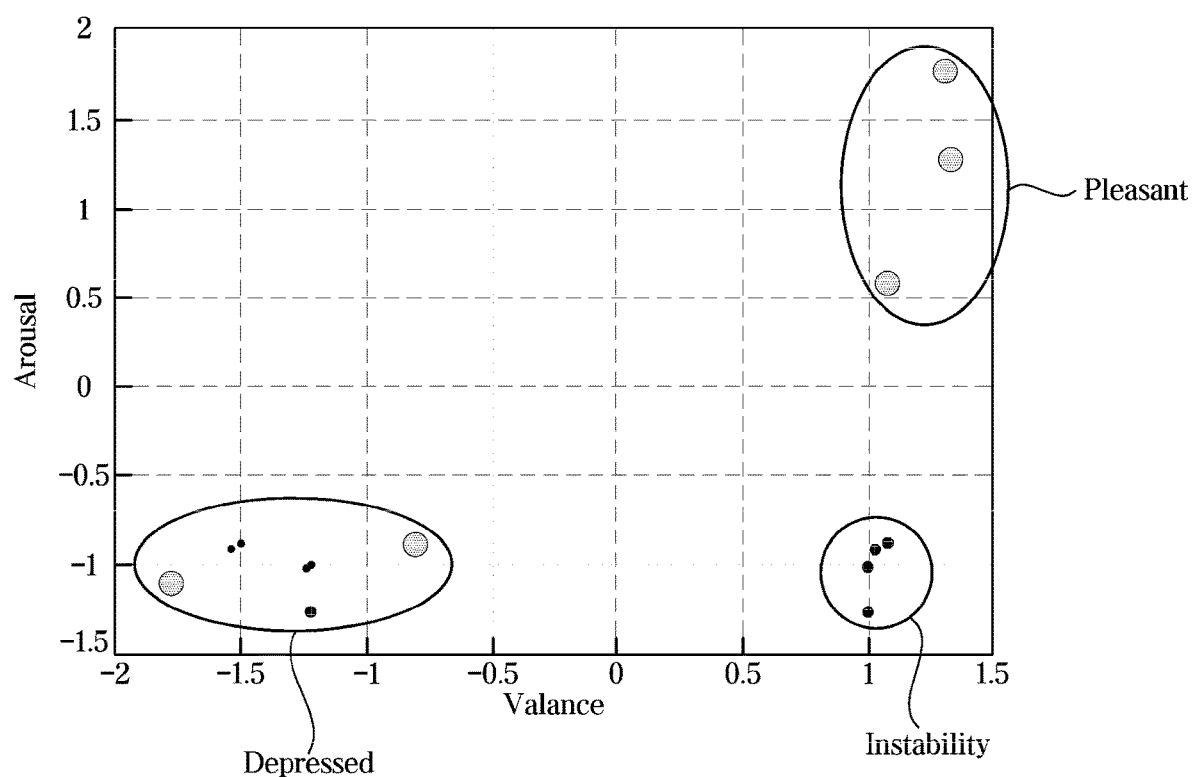

FIG. 7A is a table and FIG. 7B is a graph of emotional information of a vehicle driver according to an embodiment of the disclosure.

Referring to FIG. 7A, it is possible to identify how to change the driver's emotional information through vibration stimulation according to the seating posture.

In more detail, when the vehicle 1 controls the output device 120 to gradually fade in the vibration stimulus from a start point of the vibration stimulus, to change a vibration position, and to gradually fade out the vibration stimulus from a middle of the vibration stimulus to a stopping point, it may be identified that the driver can have a comfortable emotional state.

In addition, when the vehicle 1 controls the output device 120 so that a length of a single vibration is long, the vibration position is changed, and the intensity of the vibration is weak and gradually decreases, it may be identified that the driver can have an interesting emotional state.

In addition, when the vehicle 1 controls the output device 120 so that the intensity of the vibration is weak, the vibration stimulus from the start point of the vibration stimulus gradually fades in, and the vibration stimulus from the middle of the vibration stimulus to the stopping point gradually fades out, it may be identified that the driver can have an emotional state that the driver often wants to experience.

In addition, when the vehicle 1 controls the output device 120 so that the vibration position changes and the intensity of the vibration is weak, it may be identified that the driver can have an emotional state of stress relief.

In addition, when the vehicle 1 controls the output device 120 so that the vibration position changes, the intensity of the vibration is weak, the vibration stimulus does not gradually increase (fade in) from the starting point of the vibration stimulus, and the vibration position changes, It may be identified that the driver's preference can have a high emotional state.

In addition, when the vehicle 1 controls the output device 120 so that the vibration position changes and the intensity of the vibration is weak, it may be identified that the driver's emotion can have the positive emotional state.

In addition, when the vehicle 1 controls the output device 120 so that the vibration stimulus gradually fades in when the vibration position changes, the intensity of the vibration is strong, and there is the change in the vibration position, and the vehicle 1 controls the output device 120 so that the vibration stimulus gradually fades in when the intensity of the vibration is weak, it may be identified that the driver's emotion can have the positive emotional state.

As illustrated in FIG. 7A, the vehicle 1 may determine the driver's emotional information as three models.

Referring to FIG. 7B, the horizontal axis may represent the positive emotion, and the vertical axis may represent the arousal emotion. As the emotional index for the positive emotion and the emotional index for the arousal emotion are larger, the driver's emotional information may be emotions of excitement, happiness, and satisfaction, which are the positive emotions such Pleasant. In addition, as the emotional index for the positive emotions and the emotional index for the arousal emotions are smaller, the driver's emotional information may be emotions of irritability, depression, despair, and fear, which are the negative emotions such as Depressed.

In more detail, referring to Equation 1 below, DE is an abbreviation of Differential Entropy and represents the differential entropy value of the brain signal in theta band (4 to 8 Hz) in the central part of the frontal lobe, and theta activity in the corresponding brain region may be used as the measure to determine the arousal emotions among the driver's emotional information.

$$DE = -\int_{-\infty}^{\infty} \frac{1}{\sqrt{2\pi\sigma^2}} e^{\frac{-(x-\mu)^2}{2\sigma^2}} \log\left(\frac{1}{\sqrt{2\pi\sigma^2}} e^{\frac{-(x-\mu)^2}{2\sigma^2}}\right) dx = \frac{1}{2}\log(2\pi e \sigma^2)$$

Equation 1

Referring to Equation 2 below, FAA is an abbreviation of Frontal Alpha Asymmetry, is an index created through a phenomenon in which the alpha band EEG activity in the frontal lobe shows asymmetry in the left and right hemispheres, and the larger the positive emotion is expressed. It may be used as a measure to determine the positive emotions among the emotional information.

$$FAA = (R_{power} - L_{power})/(R_{power} + L_{power})$$

Equation 2

Figure 8:
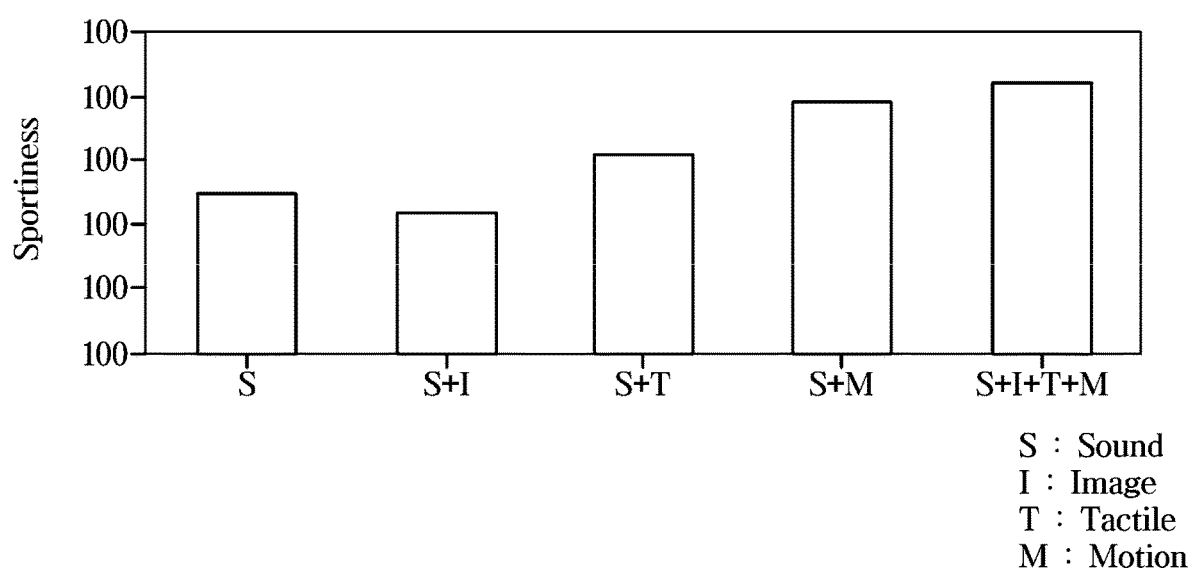
FIG. 8 is a graph of emotional information of a vehicle according to an embodiment of the disclosure.

FIG. 8 is a graph of emotional information of a vehicle according to an embodiment of the disclosure.

Referring to FIG. 8, when the vehicle 1 outputs hearing, motion, tactile sensation, and image through a seating posture analysis, it may be determined that a contribution to the driver's positive emotion is high in an order of the hearing, the motion, and the tactile sensation.

Figure 9:
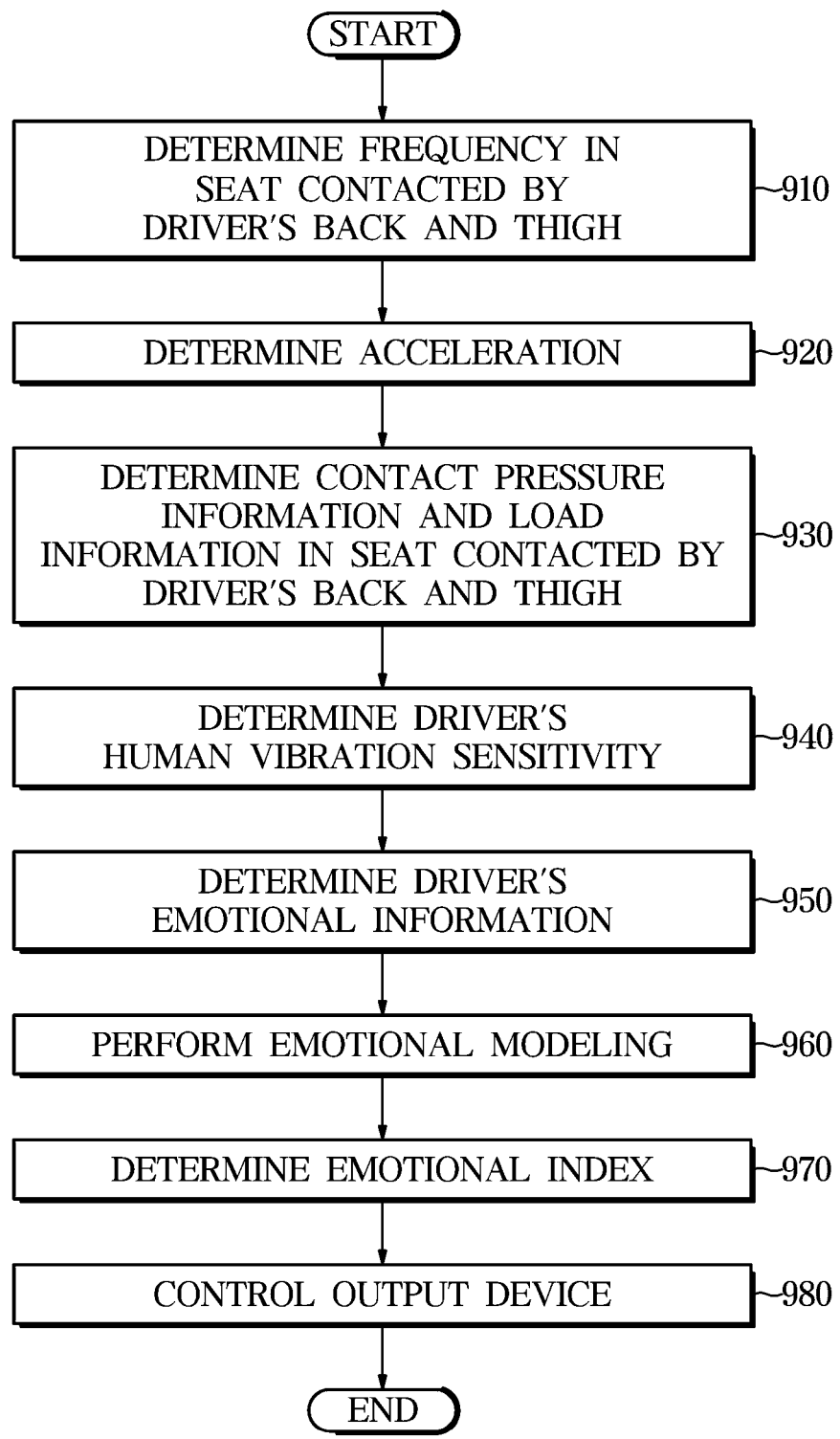
FIG. 9 is a flowchart illustrating a method of controlling a vehicle according to another embodiment of the disclosure.

FIG. 9 is a flowchart illustrating a method of controlling a vehicle according to another embodiment of the disclosure.

The vehicle 1 may obtain the frequency from each of the first seat contacted by the driver's back and the second seat contacted by the driver's thigh. In more detail, the vehicle 1 may determine the specific frequency sensitive to human vibration at 910.

The vehicle 1 may determine the acceleration in each of the first seat and the second seat through sensors attached to the first seat in contact with the driver's back and the second seat in contact with the driver's thigh at 920.

Here, the plurality of sensors 110 may be mounted on the seat of the vehicle 1 and may be the 4-axis accelerometer. In more detail, the sensors 110 may be mounted one on each of the upper and lower portions based on the center of the first seat, and the sensors 110 may be mounted on the second seat that is in contact with the driver's thigh, and one may be mounted on each of the upper, lower, left, and right sides based on the center of the second seat. However, the number of attachments and the attachment positions of the sensors 110 are not particularly limited.

The vehicle 1 may use the sensors 110 to determine the contact pressure information and the load information in the first seat contacted by the driver's back and the second seat contacted by the driver's thigh at 930.

Here, the sensors 110 may be the contact pressure measuring device, but is not limited thereto.

The vehicle 1 may determine the driver's human vibration sensitivity at 940.

In more detail, the vehicle 1 may determine the frequency sensitive to the human vibration in each of the first seat and the second seat. For example, it may be 50 Hz, 70 Hz, 90 Hz, and 110 Hz. The vehicle 1 may determine the human vibration sensitivity by using at least one of the change in the acceleration according to the frequency sensitive to the human vibration, the contact pressure information and the load information of the seat.

The vehicle 1 may determine the driver's emotional information based on the driver's human vibration sensitivity at 950.

Here, the driver's emotional information may include the positive emotional information and the arousal emotional information.

The vehicle 1 may perform the emotional modeling of the driver based on the positive emotional information and the arousal emotional information at 960.

In more detail, the vehicle 1 may perform the driver's emotional modeling using the quadrant graph having the positive emotional information as the horizontal axis and the arousal emotional information as the vertical axis. In addition, the vehicle 1 may perform the emotional modeling by setting the moving pattern in each quadrant of the quadrant graph so that the driver's emotional information changes to the positive emotional information.

The vehicle 1 may determine the emotional index of the driver's emotional information at 970.

In this case, the vehicle 1 may determine the driver's EEG information and the HRV in order to determine the driver's emotional index.

The vehicle 1 may use the HRV analysis method to determine the driver's heart rate fluctuation.

In more detail, the vehicle 1 may use the FAA-Valence analysis method as the measure of the positive emotion among the driver's emotional information for the emotional index analysis.

In addition, the vehicle 1 may use the FTDE-Arousal analysis method as the measure of the arousal emotion among the driver's emotional information for the emotional index analysis.

In more detail, as the emotional index for the positive emotion and the emotional index for the arousal emotion are larger, the driver's emotional information may be emotions of excitement, happiness, and satisfaction, which are the positive emotions such Pleasant. In addition, as the emotional index for the positive emotions and the emotional index for the arousal emotions are smaller, the driver's emotional information may be emotions of irritability, depression, despair, and fear, which are the negative emotions such as Depressed.

The vehicle 1 may control the output device 120 based on at least one of the driver's emotional information, the emotional modeling, and the emotional index at 980.

In more detail, the vehicle 1 may control the speaker 121 to output the sound in order to change the driver's emotion into the positive emotion.

The vehicle 1 may control the haptic generator 122 and the vibrator 123 to change the driver's emotion into the positive emotion, and control the output of the ultrasonic waves or the vibrations. Here, the vibrator 123 may include the actuator, the plurality of vibrators 123 may be mounted on the seat of the vehicle 1.

The vehicle 1 may simultaneously output the sound, the vibration, and the ultrasound, and may automatically output the sound, the vibration, and the ultrasound by setting the output time of the sound, the vibration, and the ultrasound based on the driver's emotional information and emotional modeling.

The vehicle 1 may smoothly control the steering wheel of the vehicle 1 so that the driver's emotion changes into the positive emotion.

According to the embodiments of the disclosure, the vehicle 1 may apply a high-performance vehicle Electronic Sound Generator (ESG) sound.

In the embodiments of the disclosure, the vehicle 1 may be applied with a Vibro Music Seat, Massage Seat, and Sound Therapy of an electric vehicle.

According to the embodiments of the disclosure, the vehicle 1 may apply a SubPack of an autonomous vehicle.

According to the embodiments of the disclosure, there is an effect of improving marketability as the vehicle in consideration of the driver's emotions.

In addition, there is an effect of minimizing development costs by enabling cost reduction through software and algorithm implementation and compatibility by all vehicle types.

The disclosed embodiments may be implemented in the form of a recording medium storing computer-executable instructions that are executable by a processor. The instructions may be stored in the form of a program code, and when executed by a processor, the instructions may generate a program module to perform operations of the disclosed embodiments. The recording medium may be implemented non-transitory as a non-transitory computer-readable recording medium.

The non-transitory computer-readable recording medium may include all types of recording media storing commands that may be interpreted by a computer. For example, the non-transitory computer-readable recording medium may be, for example, ROM, RAM, a magnetic tape, a magnetic disc, flash memory, an optical data storage device, and the like.

Embodiments of the disclosure have thus far been described with reference to the accompanying drawings. It should be apparent to those of ordinary skill in the art that the disclosure may be practiced in other forms than the embodiments as described above without changing the technical idea or essential features of the disclosure. The above embodiments are only by way of example, and should not be interpreted in a limited sense.

The invention claimed is:

1. A vehicle comprising:
   a plurality of sensors mounted on a seat;
   an output device; and
   a controller configured to:
   obtain an acceleration in each of a first seat in contact with a driver's back and a second seat in contact with a driver's thigh through the plurality of sensors;
   determine a specific frequency in each of the first seat and the second seat;
   determine contact pressure information and load information of each of the first seat and the second seat via the plurality of sensors;
   determine a human vibration sensitivity using at least one of the specific frequency, the contact pressure information, and the load information;
   determine driver's emotional information including positive emotional information and arousal emotional information based on the human vibration sensitivity; and
   control the output device according to the driver's emotional information;

wherein the controller is further configured to perform an emotional modeling based on the driver's emotional information;

wherein the controller is further configured to perform the emotional modeling using a quadrant graph having the positive emotional information as a horizontal axis and the arousal emotional information as a vertical axis;

wherein the controller is further configured to set a moving pattern in each quadrant of the quadrant graph so the driver's emotional information changes to the positive emotional information; and wherein, in response to a case where the driver's emotional information is one of a pattern moving from a second quadrant to a first quadrant, a pattern moving from the second quadrant to a fourth quadrant, a pattern moving from a third quadrant to the first quadrant, and a pattern moving from the third quadrant to the fourth quadrant, the controller is configured to determine that a driver's emotion changes to a positive emotion.

2. The vehicle according to claim 1, wherein the controller is further configured to measure driver's electroencephalogram (EEG) information and a driver's heart rate.

3. The vehicle according to claim 2, wherein the controller is further configured to reflect the EEG information and the heart rate to determine an emotional index of the emotional information.

4. The vehicle according to claim 3, wherein the controller is further configured to:
determine that as the emotional index for the positive emotional information and the emotional index for the arousal emotional information increase, the driver's emotional information is the positive emotional information; and
determine that as the emotional index for the positive emotional information and the emotional index for the arousal emotional information decrease, the driver's emotional information is negative emotional information.

5. The vehicle according to claim 1, wherein the output device comprises at least one of a speaker, the seat, and a steering wheel.

6. The vehicle according to claim 1, wherein the specific frequency is a frequency sensitive to a human vibration.

7. A method of controlling a vehicle comprising:
obtaining, by a controller, an acceleration in each of a first seat in contact with a driver's back and a second seat in contact with a driver's thigh via a plurality of sensors;
determining, by the controller, a specific frequency in each of the first seat and the second seat;
determining, by the controller, contact pressure information and load information of each of the first seat and the second seat through the plurality of sensors;
determining, by the controller, a human vibration sensitivity using at least one of the specific frequency, the contact pressure information, and the load information;
determining, by the controller, driver's emotional information including positive emotional information and arousal emotional information based on the human vibration sensitivity;
controlling, by the controller, an output device according to the driver's emotional information;
performing, by the controller, an emotional modeling based on the driver's emotional information;
performing, by the controller, the emotional modeling using a quadrant graph having the positive emotional information as a horizontal axis and the arousal emotional information as a vertical axis;
setting, by the controller, a moving pattern in each quadrant of the quadrant graph so the driver's emotional information changes to the positive emotional information; and
in response to a case where the driver's emotional information is one of a pattern moving from a second quadrant to a first quadrant, a pattern moving from the second quadrant to a fourth quadrant, a pattern moving from a third quadrant to the first quadrant, and a pattern moving from the third quadrant to the fourth quadrant, determining, by the controller, that a driver's emotion changes to a positive emotion.

8. The method according to claim 7, further comprising:
measuring, by the controller, driver's electroencephalogram (EEG) information and a driver's heart rate.

9. The method according to claim 8, further comprising:
reflecting, by the controller, the EEG information and the heart rate to determine an emotional index of the emotional information.

10. The method according to claim 9, further comprising:
determining, by the controller, that as the emotional index for the positive emotional information and the emotional index for the arousal emotional information increase, the driver's emotional information is the positive emotional information; and
determining, by the controller, that as the emotional index for the positive emotional information and the emotional index for the arousal emotional information decrease, the driver's emotional information is negative emotional information.

11. The method according to claim 7, wherein the output device comprises at least one of a speaker, the seat, and a steering wheel.

12. The method according to claim 7, wherein the specific frequency is a frequency sensitive to a human vibration.

* * * * *